US008266738B2

(12) United States Patent
Castellote et al.

(10) Patent No.: US 8,266,738 B2
(45) Date of Patent: Sep. 18, 2012

(54) AROMATHERAPY SYSTEM FOR TUBS

(75) Inventors: Miguel A. Castellote, Sainte-Marguerite de Dorchester (CA); Dominique Ciechanowski, Sainte-Marguerite de Dorchester (CA)

(73) Assignee: C. G. Air Systems Inc., Sainte-Marguerite Dorchester (CA)

( * ) Notice: Subject to any disclaimer, the term of this patent is extended or adjusted under 35 U.S.C. 154(b) by 684 days.

(21) Appl. No.: 12/339,417

(22) Filed: Dec. 19, 2008

(65) Prior Publication Data
US 2009/0158519 A1  Jun. 25, 2009

Related U.S. Application Data

(60) Provisional application No. 61/015,739, filed on Dec. 21, 2007.

(51) Int. Cl.
*A47K 3/00* (2006.01)
(52) U.S. Cl. ............................................ 4/559; 239/302
(58) Field of Classification Search ...................... 4/559; 239/301–311, 427, 398; 261/77
See application file for complete search history.

(56) References Cited

U.S. PATENT DOCUMENTS

| 4,215,082 | A | * | 7/1980 | Danel ........................... 261/124 |
| 4,504,388 | A | * | 3/1985 | Desbos et al. ................. 210/130 |
| 4,564,480 | A | * | 1/1986 | Kamelmacher .............. 261/36.1 |
| 2002/0148911 | A1 | * | 10/2002 | Beck et al. ..................... 239/310 |
| 2005/0217016 | A1 | * | 10/2005 | Ciechanowski et al. .......... 4/559 |

FOREIGN PATENT DOCUMENTS

CA  2430862  *  1/2004
* cited by examiner

*Primary Examiner* — Gregory Huson
*Assistant Examiner* — Karen L Younkins
(74) *Attorney, Agent, or Firm* — Norton Rose Canada LLP

(57) ABSTRACT

An assembly of an aromatherapy system and tub comprises a tub for bathing. A reservoir portion contains an aromatic liquid, the reservoir portion being mounted to a wall of the tub. A pressure source is actuatable to provide pressurized gas, the pressure source being concealed under the tub. A fluid-conveying line is concealed under the tub and connecting the pressure source to the reservoir portion to diffuse the pressurized gas from the pressure source into the aromatic liquid in the reservoir portion so as to create a mist of the aromatic liquid in the environment of the tub.

9 Claims, 2 Drawing Sheets

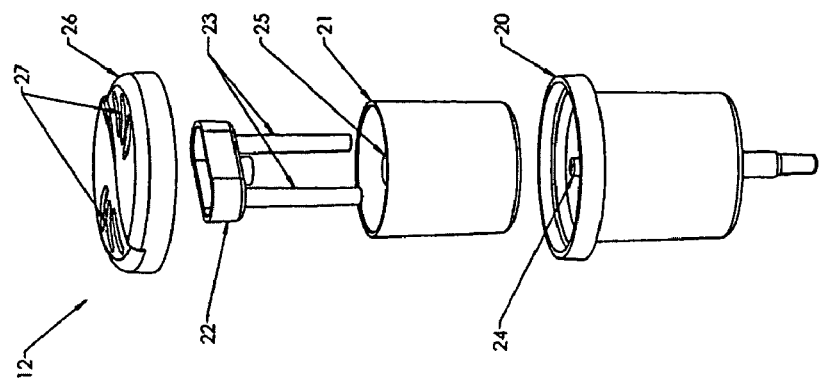
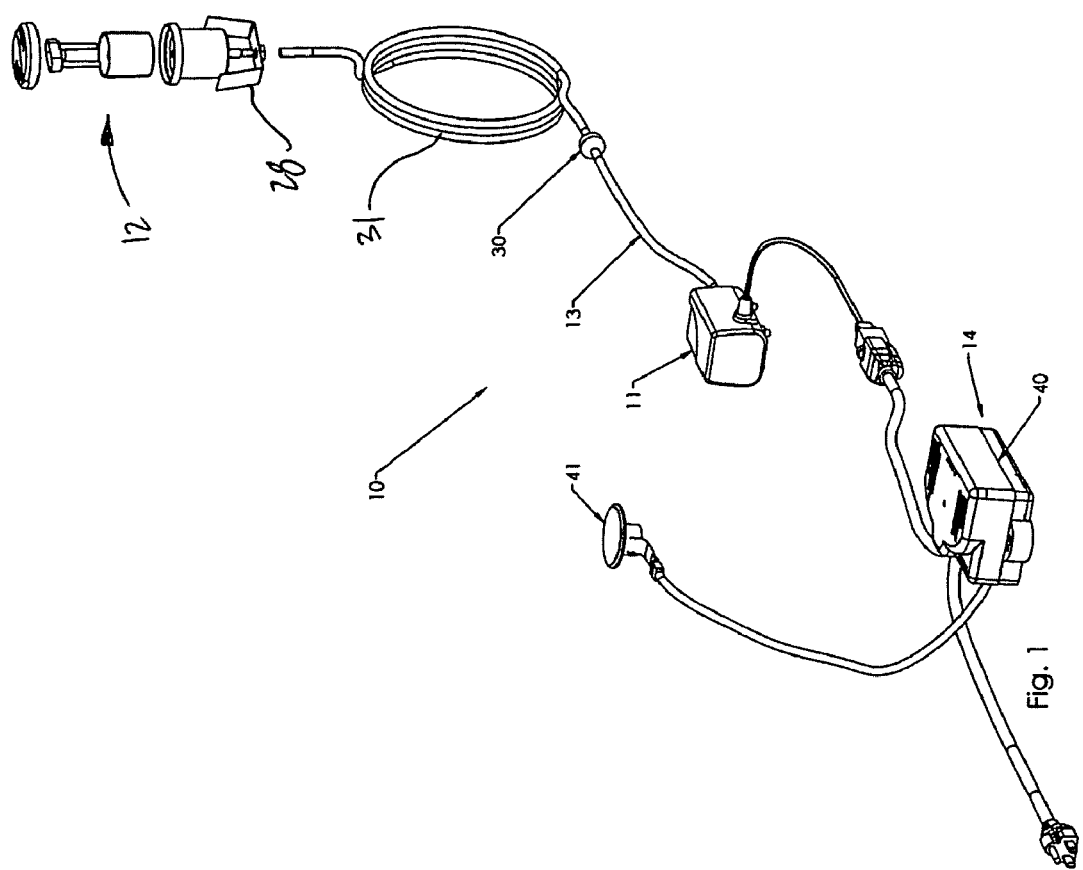
Fig. 2
Fig. 1

AROMATHERAPY SYSTEM FOR TUBS

CROSS-REFERENCE TO RELATED APPLICATION

This patent application claims priority on U.S. Provisional Patent Application No. 61/015,739, filed on Dec. 21, 2007.

FIELD OF THE APPLICATION

The present application relates to washing/bathing tub accessories and, more particularly, to an aromatherapy system to be used in conjunction with tubs, such as bathtubs, spas, pools, etc.

BACKGROUND OF THE ART

Tubs are well known for their primary use, namely a washroom installation in which a user person washes, bathes. Tubs have, however, evolved to add relaxation and comfort to practicality, and are found in many forms, such as bathtubs, spas, whirlpools. For instance, tubs are now provided with air-jet systems and whirlpool systems.

In order to increase the level of relaxation of bathers, there are provided systems that enhance the senses of the bather. Bathing typically procures stimulation of the sense of touch, by the temperature and feel of the water on the skin. The air-jet systems and whirlpool systems increase the stimulation of the sense of touch by creating turbulences in the vicinity of the skin of the bather.

Various systems and apparatuses are used in order to involve other senses during the bathing period. For instance, waterproof radios and the like are more present adjacent to bathtubs. Aromatic oils come in numerous aromas. The tubs, however, remain limited in the enhancement of other senses.

SUMMARY OF THE APPLICATION

It is therefore an aim of the present application to provide a novel aromatherapy system.

Therefore, in accordance with the present application, there is provided an aromatherapy system for tubs comprising a reservoir portion containing an aromatic liquid; a pressure source providing pressurized gas; and means for diffusing the pressurized gas from the pressure source in the reservoir portion so as to create a mist of the aromatic liquid.

BRIEF DESCRIPTION OF THE DRAWINGS

FIG. 1 is a perspective view of an aromatherapy system constructed in accordance with an embodiment of the present application FIG. 2 is an enlarged assembly view of a reservoir portion of the aromatherapy system of FIG. 1.

DESCRIPTION OF THE PREFERRED EMBODIMENTS

Figure 3:
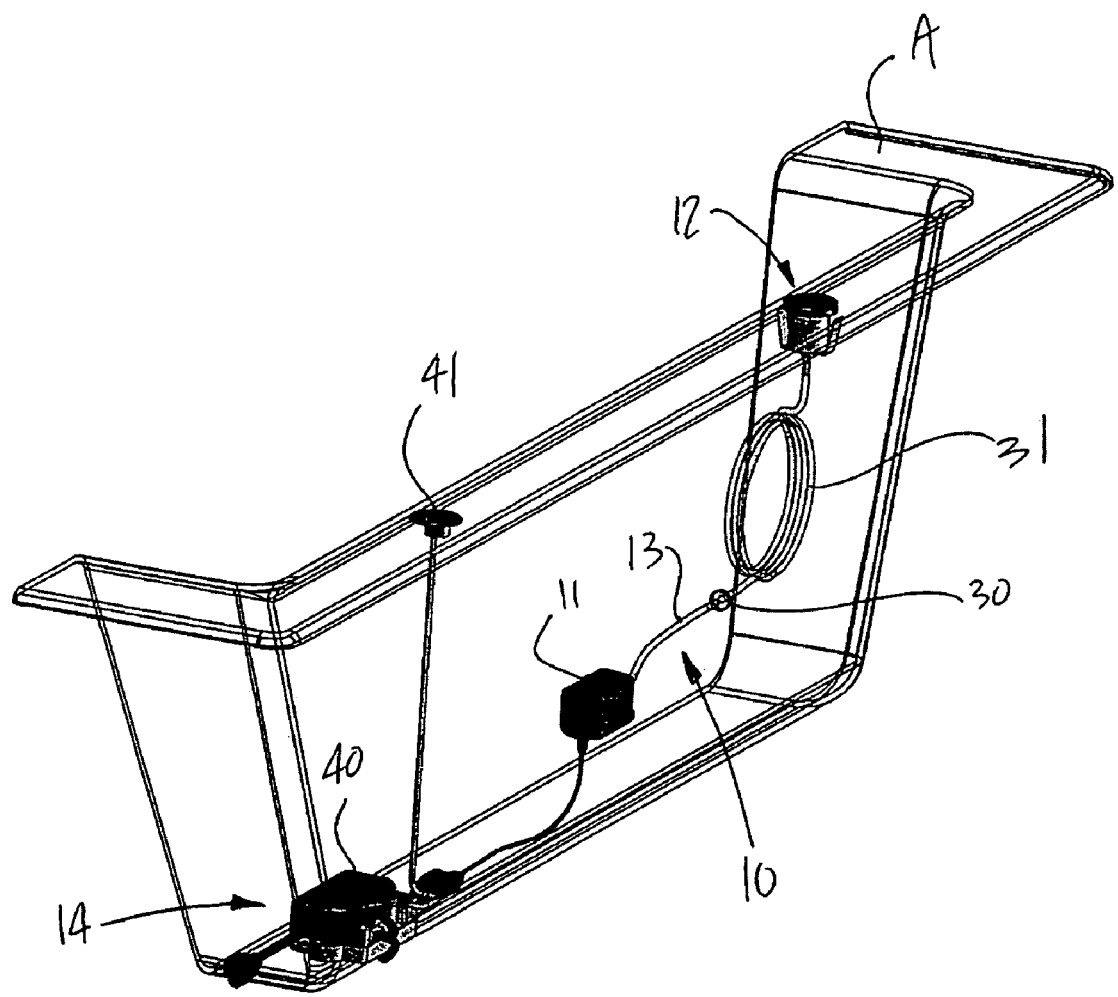
FIG. 3 is a perspective view of the aromatherapy system of FIG. 1 as partially concealed under a tub.

Referring to FIG. 1, an aromatherapy system in accordance with an embodiment is generally shown at 10. The aromatherapy system 10 produces an aromatic mist in the tub environment.

In order to produce the aromatic mist, the aromatherapy system 10 has a pressure source 11, a reservoir portion 12, piping or fluid-conveying line 13, and a controller portion 14.

The pressure source 11 produces a flow of air or gas to vaporize an aromatic liquid. The pressure source 11 is for instance an air compressor, a blower or other like pressure sources.

As illustrated in FIG. 3, the reservoir portion 12 may be mounted to the tub or is in the vicinity of the tub A, and contains the aromatic liquid that will be vaporized into an aromatic mist.

Referring to FIG. 1, piping 13 interrelates the pressure source 11 to the reservoir portion 12. The piping 13 may be tubing, pipes, ducts, or the like.

The controller portion 14 controls the operation of the aromatherapy system 10, for instance in accordance with the commands of a user portion.

Referring concurrently to FIGS. 1-3, the reservoir portion 12 has a support 20 and a liquid reservoir 21. The support 20 is the interface between a support wall of a tub A or tub surroundings, and the liquid reservoir 21. The support 20 may be seated on the periphery of a hole in the tub A, and is secured thereto.

The liquid reservoir 21 is provided to contain the aromatic fluid. The liquid reservoir 21 is accessible by the user person, for manual refill of aromatic liquid in the reservoir 21.

A manifold 22 is positioned within the liquid reservoir 21, and has a pair of arms 23. The arms 23 project downwardly into the pool of aromatic liquid, so as to blow air therein to vaporize the aromatic liquid. The manifold 22 may have one or more arms 23.

In order to direct air from the pressure source 11 to the arms 23, the piping 13 is connected at one end to the pressure source 11, and at another end to a conduit 24 in the support 20. The conduit 24 extends upwardly in the support 20 to reach the manifold 22. The liquid reservoir 21 features a tubular member 25 allowing the conduit 24 to pass therethrough to reach the manifold 22.

A cover member 26 is releasably secured to the support 20, for instance by way of snap-fitting engagement, threading engagement, or the like. The cover member 26 has a plurality of vents 27, which allow the aromatic mist to exit the liquid reservoir 21.

Referring concurrently to FIGS. 1 and 3, a U-shaped bracket 28 may be used to secure the support 20 to the hidden surface of the tub A. The bracket 28 is used in combination with a fastener that is screwed to a bottom of the conduit 24, to urge the support 20 against the tub A.

Although the reservoir portion 12 is described and illustrated as having an assembly of the support 20, the liquid reservoir 21 and the manifold 22 held together with a cover member 26, some of these components may be combined. For instance, the support 20 may act as reservoir. Similarly, the manifold may be a nozzle provided in the bottom of the support 20 or of the liquid reservoir 21.

Therefore, pressurized air/gas from the pressure source 11 passes through piping 13, reaching the conduit 24. From the conduit 24, the air/gas will be fed to the manifold 22 and into the arms 23. Once out of the arms 23, the gas/air will bubble into the aromatic liquid in the liquid reservoir 21. An aromatic mist will result from the bubbling, which aromatic mist exits the reservoir portion 12 through the vents 27 in the cover member 26.

It is pointed out that the body of the manifold 22, from which project the arms 23, is above a liquid level in the liquid reservoir 21. This generally prevents liquid from entering the manifold 22 and hence potentially reaching the pressure source 11.

A check valve 30 is part of the piping 13. The check valve 30 is used to prevent water reaching the pressure source 11.

Moreover, although not illustrated in FIG. 1, it is considered to install the piping 13 in a Hartford loop configuration 31 as an additional safety measure.

The controller portion 14 has a controller 40 and a keypad 41 (e.g., switch, keypad, interface). The controller 40 relates the pressure source 11 to a power source by way of appropriate wiring as illustrated in FIG. 1.

The keypad 41 is the interface by which the user person operates the aromatherapy system 10. The keypad 41 typically offers basic functions, such as on/off. It is considered to provide additional commands and information with the keypad 41. It is also considered to use the keypad of an existing tub system (e.g., an air massage system, water massage system, chromotherapy, etc.).

Referring to FIG. 3, a part of the reservoir portion 12 (e.g., the cover member 26, and upper ends of other components) and the keypad 41 are shown as being visible from an exposed side of the tub A. On the other hand, the pressure source, the piping 13, the controller 40 as well as wires are concealed under the tub A, and therefore do not affect the visual aspect of the tub A.

Although the aromatherapy system 10 is preferably secured to an opening in a wall of the tub, the aromatherapy system 10 may be a self-contained system adjacent to the tub, or part of furniture, such as cabinet. The aromatherapy system 10 may also be mounted to a shelf, a counter or any other like surface. The tub is typically any one of a bathtub, a spa, a pool, a basin.

Different aromatic liquids/gels/solids can be used with the aromatherapy system 10, but for simplicity purposes reference is made above to aromatic liquids. In a non-restrictive embodiment, the aromatic liquid is a mixture of water and essential oils.

The invention claimed is:

1. An aromatherapy system for tubs comprising:
   a reservoir portion comprising:
      a support adapted to be secured to a tub wall,
      a reservoir member accommodated in the support and defining a vessel for containing an aromatic liquid, the reservoir member having a generally upward tubular portion projecting upwardly from a bottom of the vessel to provide the vessel with an annular shape,
      a manifold positioned above a level of the aromatic liquid in the reservoir member, the manifold having at least one arm projecting into the aromatic liquid to direct pressurized gas into the aromatic liquid;
   a pressure source being actuatable to provide pressurized gas; and
   a fluid-conveying line connecting the pressure source to the manifold of the reservoir portion to diffuse the pressurized gas from the pressure source into the aromatic liquid in the reservoir portion so as to create a mist of the aromatic liquid in the environment of the tub, the fluid-conveying line being in fluid communication with the manifold via the tubular portion of the reservoir member.

2. The aromatherapy system according to claim 1, wherein the manifold has a pair of said arms.

3. The aromatherapy system according to claim 1, wherein the support has a conduit passing through the tubular portion to be connected to the manifold, the fluid-conveying line being connected to the conduit for supplying pressurized gas to the conduit.

4. The aromatherapy system according to claim 1, further comprising a cover member releasably secured to the reservoir portion, and having vent slots for the mist to flow out of the reservoir portion.

5. An assembly of an aromatherapy system and tub comprising:
   a tub for bathing;
   a reservoir portion comprising:
      a support adapted to be secured to a tub wall,
      a reservoir member accommodated in the support and defining a vessel for containing an aromatic liquid, the reservoir member having a generally upward tubular portion projecting upwardly from a bottom of the vessel to provide the vessel with an annular shape,
      a manifold positioned above a level of the aromatic liquid in the reservoir member, the manifold having at least one arm projecting into the aromatic liquid to direct pressurized gas into the aromatic liquid;
   a pressure source being actuatable to provide pressurized gas, the pressure source being concealed under the tub; and
   a fluid-conveying line concealed under the tub and connecting the pressure source to the manifold of the reservoir portion to diffuse the pressurized gas from the pressure source into the aromatic liquid in the reservoir portion so as to create a mist of the aromatic liquid in the environment of the tub, the fluid-conveying line being in fluid communication with the manifold via the tubular portion of the reservoir member.

6. The assembly according to claim 5, further comprising an interface mounted to a wall of the tub for controlling the pressure source.

7. The assembly according to claim 5, wherein the manifold has a pair of said arms.

8. The assembly according to claim 5, wherein the support has a conduit passing through the tubular portion to be connected to the manifold, the line being connected to the conduit for supplying pressurized gas to the conduit.

9. The assembly according to claim 5, further comprising a cover member releasably secured to the reservoir portion, and having vent slots for the mist to flow out of the reservoir portion.

* * * * *